(12) United States Patent
Carlsson et al.

(10) Patent No.: US 10,285,850 B2
(45) Date of Patent: May 14, 2019

(54) HOLDING ELEMENT FOR AN ACTIVE ARTICLE OF CLOTHING

(71) Applicant: INUHEAT GROUP AB, Billdal (SE)

(72) Inventors: Stefan Carlsson, Bjarred (SE); Rickard Rosendahl, Kullavik (SE)

(73) Assignee: Inuheat Group AB, Billdal (SE)

( * ) Notice: Subject to any disclaimer, the term of this patent is extended or adjusted under 35 U.S.C. 154(b) by 206 days.

(21) Appl. No.: 15/524,934

(22) PCT Filed: Nov. 6, 2015

(86) PCT No.: PCT/SE2015/051176
§ 371 (c)(1),
(2) Date: May 5, 2017

(87) PCT Pub. No.: WO2016/072925
PCT Pub. Date: May 12, 2016

(65) Prior Publication Data
US 2017/0319379 A1 Nov. 9, 2017

(30) Foreign Application Priority Data
Nov. 6, 2014 (SE) ...................................... 1451321

(51) Int. Cl.
*A61F 7/00* (2006.01)
*H05B 3/34* (2006.01)
(Continued)

(52) U.S. Cl.
CPC .............. *A61F 7/007* (2013.01); *A41D 1/005* (2013.01); *A41D 13/0051* (2013.01); *H05B 3/34* (2013.01);
(Continued)

(58) Field of Classification Search
None
See application file for complete search history.

(56) References Cited

U.S. PATENT DOCUMENTS

| 2,287,915 A | 6/1942 | Taylor |
| 3,407,818 A | 10/1968 | Costanzo |
| (Continued) | | |

FOREIGN PATENT DOCUMENTS

| DE | 102011007419 | 10/2012 |
| EP | 1705956 | 9/2006 |
| (Continued) | | |

OTHER PUBLICATIONS

International Search Report for PCT/SE2015/051176, Cpmpleted by the Swedish Patent Office on Mar. 4, 2016, 5 Pages.
(Continued)

*Primary Examiner* — John Fox
(74) *Attorney, Agent, or Firm* — Brooks Kushman P.C.

(57) ABSTRACT

A holding element is intended to be affixed to an active article of clothing at two spaced apart locations. It is provided with first electrical terminals for connection to an activation unit, which is to be secured to the article of clothing by the holding element, second electrical terminals for connection to a functional component of the active article of clothing and electrically conductive paths between the first and second terminals, the second electrical terminals being placed where the holding element is intended to be affixed to the article of clothing. The holding element is arranged to hold the activation unit between the holding element and the article of clothing between the two spaced apart locations and the holding element is flexible so that it shapes itself around the activation unit when the activation unit is introduced between the holding element and the article of clothing.

12 Claims, 3 Drawing Sheets

(51) Int. Cl.
*A41D 13/005* (2006.01)
*A41D 1/00* (2018.01)
*A61F 7/02* (2006.01)

(52) U.S. Cl.
CPC ........ *H05B 3/342* (2013.01); *A61F 2007/008* (2013.01); *A61F 2007/0045* (2013.01); *A61F 2007/0233* (2013.01); *H05B 2203/036* (2013.01)

(56) References Cited

U.S. PATENT DOCUMENTS

| | | | |
|---|---|---|---|
| 3,632,966 A | | 1/1972 | Arron |
| 4,087,675 A | | 5/1978 | Sansonetti |
| 4,764,655 A | | 8/1988 | Orban et al. |
| 4,950,868 A | * | 8/1990 | Moss ................. A41D 13/0051 219/211 |
| 5,541,388 A | | 7/1996 | Gadd |
| 6,268,595 B1 | * | 7/2001 | Haenel ...................... A61F 7/02 219/211 |
| 6,319,015 B1 | * | 11/2001 | Faunce ................. H01R 11/22 24/662 |
| 6,563,424 B1 | | 5/2003 | Kaario |
| 2007/0055330 A1 | | 3/2007 | Rutherford |
| 2007/0095808 A1 | | 5/2007 | Lacy, III |
| 2007/0278201 A1 | * | 12/2007 | Jones ..................... A41B 11/00 219/211 |
| 2008/0142060 A1 | | 6/2008 | Orth et al. |
| 2009/0056107 A1 | | 3/2009 | Williams |
| 2009/0188905 A1 | | 7/2009 | Williams |
| 2011/0049117 A1 | * | 3/2011 | Macher ............ A41D 19/01535 219/211 |
| 2012/0193342 A1 | | 8/2012 | Macher et al. |
| 2013/0306614 A1 | * | 11/2013 | Fey, Jr. .................... A41D 1/00 219/211 |
| 2015/0083704 A1 | * | 3/2015 | Guidry ............ A41D 19/01535 219/211 |
| 2016/0249695 A1 | | 9/2016 | Clemente |

FOREIGN PATENT DOCUMENTS

| | | |
|---|---|---|
| EP | 1801684 | 6/2007 |
| WO | 2008062193 | 5/2008 |

OTHER PUBLICATIONS

Extended European Search Report for European Application No. EP15856910.3, dated Apr. 3, 2018, 7 Pages.

* cited by examiner

HOLDING ELEMENT FOR AN ACTIVE ARTICLE OF CLOTHING

CROSS-REFERENCE TO RELATED APPLICATION

This application is the U.S. national phase of PCT Application No. PCT/SE2015/051176 filed on Nov. 6, 2015, which claims priority to SE Patent Application No. 1451321-2 filed on Nov. 6, 2014, the disclosures of which are incorporated in their entirety by reference herein.

TECHNICAL FIELD

The invention relates to a holding element for an active article of clothing, an active article of clothing provided with such a holding element and a kit comprising an active article of clothing and an activation unit.

BACKGROUND ART

Actively heated garments, to which heat is supplied in addition to the heat generated by the body, have gained increased popularity in recent years. Another trend within the clothing industry is to incorporate sensors for measurement of body functions in garments worn close to the body. Such garments, which include added functionality in comparison to that of traditional garments, can be described as active garments or active articles of clothing.

One example of an active article of clothing is shown in US 2012/0193342, which relates to an electrically heatable sock. A heating element is disposed in the foot part and connected via electrical wires to terminals for a power source for the heating. The terminals are located at a cuff of the sock. In order to secure the power source to the sock, the power source is held against the upper region of the leg part of the sock and the cuff is folded over an upper region of the leg part so that the terminals on the cuff are connected to the terminals of the power source. The power source is retained in place partly by the connected terminals and partly by the folded-over cuff. This solution for securing the power source to the garment is specific for a sock and can hardly be used for other kinds of garments.

Another example of an active article of clothing is found in EP1705956, which shows an electrically heated vest where a power source is placed in a designated pocket in the vest. The power source is provided with two electrical wires, each of which is connected to a terminal attached to a conductive portion of the vest. The electrical wires extending from the power source in the pocket to the terminals on the vest risk to get caught in projecting objects so that the power supply is unintentionally removed from the pocket. Also, the provision of a pocket and terminals on the vest implies that the manufacturing process has to be modified, something that usually leads to increased costs.

U.S. Pat. No. 3,407,818 discloses an active article of clothing in the form of an electrical heating belt. Batteries for providing power to the belt are carried by a pouch. The pouch is secured to the belt by means of a loop through which the belt can be threaded and by means of snap contacts. The batteries are carried inside the pouch and supported by the bottom and the walls of the pouch. The batteries are electrically connected to the pouch through a pair of contacts in the flap which defines the top portion of the pouch. Wire conductors are connected between the flap contacts and the snap contacts at the back of the pouch. This solution is specific to a belt and cannot be used on other articles of clothing.

SUMMARY

It is an objective of the invention to at least partly overcome one or more limitations of the prior art.

Another objective is to provide improved means for securing and electrically connecting an activation unit to an active article of clothing.

One or more of these objectives, as well as further objectives that may appear from the description below, are at least partly achieved by a holding element according claim 1, an active article of clothing according to claim 9 and a kit according to claim 12, embodiments thereof being defined by the dependent claims.

A holding element according to the invention is intended to be affixed to an active article of clothing at two spaced apart locations. The holding element is provided with first electrical terminals for connection to an activation unit, which is to be secured to the article of clothing by the holding element, second electrical terminals for connection to at least one component of the active article of clothing that is intended to be electrically connected to the activation unit, and electrically conductive paths between the first and second electrical terminals. The second electrical terminals are placed where the holding element is intended to be affixed to the article of clothing. The holding element is arranged to hold the activation unit between the holding element and the article of clothing between the two spaced apart locations; and the holding element is flexible so that it shapes itself around the activation unit when the activation unit is introduced between the holding element and the article of clothing.

The holding element can be manufactured separately from the article of clothing and affixed thereto afterwards. In this way, the manufacturing process for the article of clothing may not need to be modified. Since the holding element includes electrically conductive paths, no loose wires are needed for the transfer of electricity between the actuation unit held by the holding element and the article of clothing. The holding element can be used on different places on most types of garments.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

DETAILED DESCRIPTION OF EXAMPLE EMBODIMENTS

The following description will refer to articles of clothing that could be described as being "active" in the sense that they include additional functionality compared to traditional passive articles of clothing and they include functional components that are intended to be electrically connected to an activation unit.

An activation unit is a unit that activates the added functionality of an active article of clothing. It may be implemented as a powering unit that powers a functional component of the active article of clothing or a control unit that sends and/or receives electrical signals to and/or from the functional component of the active article of clothing, or a combination thereof.

The functional component may for instance be a heating element, a cooling element, a sensor, a stimulator, or an audio- or light-emitting component.

The expression "article of clothing" shall be broadly interpreted as including different kind of garments or apparels or wearables that are used by humans or animals. It is also intended to include other garment-like elements, like blankets and bandages, that are applied on the body for instance for comfort and/or therapeutic or diagnostic purposes.

Figure 1A:
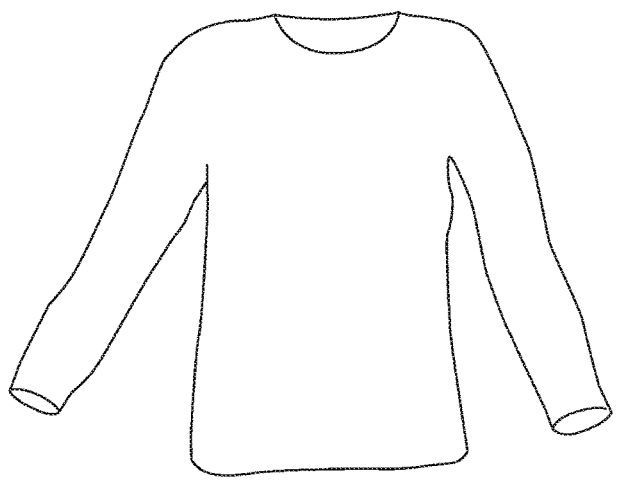
FIGS. 1A-1D show examples of articles of clothing that may be of an active type.
Figure 1B:
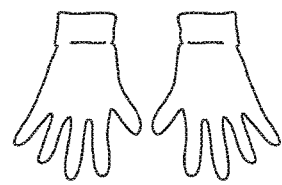
Figure 1C:
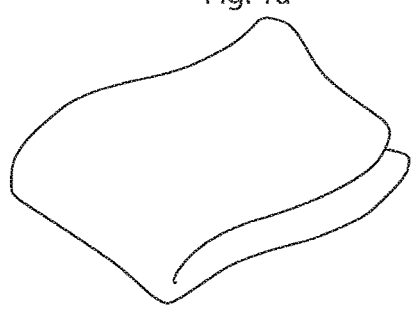
Figure 1D:
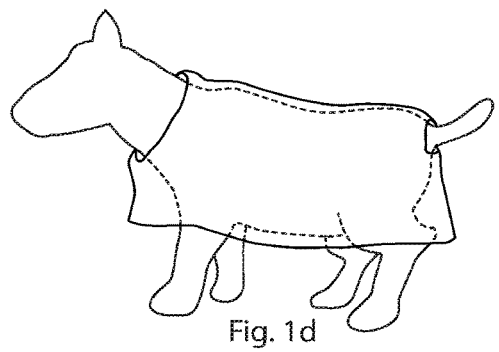

The active articles of clothing are preferably worn in direct contact with the skin of the body. FIGS. 1A-1D show different examples of articles of clothing that can be of the active type, for instance prepared for active heating. FIG. 1A is a long-sleeved base-layer shirt, FIG. 1B is a glove, FIG. 1C is a blanket, and FIG. 1D is a coat carried by a dog. Other non-exhaustive examples of articles of clothing that may be prepared for being active are socks, undergarments, base-layer pants, caps, scarves, and sport gears that are worn like an article of clothing, such as a back protector.

Figure 2:
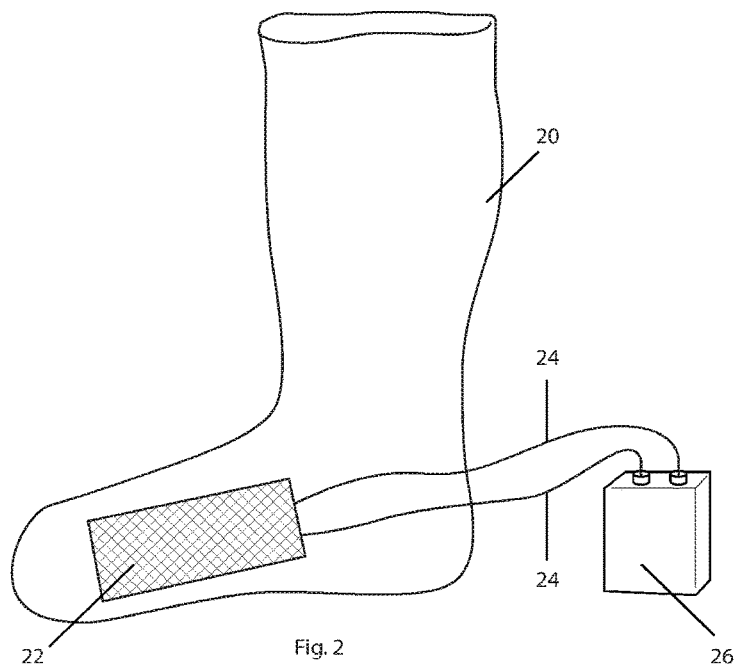
FIG. 2 is a schematic drawing that illustrates the general principles for an active article of clothing, FIG. 3 schematically shows how an activation unit is held by a holding element.

FIG. 2 schematically illustrates the principles for an active article of clothing, which in this example is an actively heated sports sock 20. The sock includes a heating element 22 which provides the heat for warming up the user and which is powered via electrical wires 24 from an activation unit 26 in the form of a battery.

The heating element 22 may be a separate element, arranged for instance between two layers of sock material in the foot part. It may however also be an integrated part of the article of clothing. In knitted or woven articles of clothing, a heating element may be provided by means of electrically conductive threads or thread-like elements that are knitted or woven into the portion of the article of clothing that is to act as a heating element. As another example, the heating element may be achieved by coating a part of the article of clothing by an electrically conductive material. Yet another alternative may be to sew electrically conductive seams onto the article of clothing.

The electrical wires 24 may also be separate from the article of clothing itself or integrated therewith. They may consist of electrically conductive threads or thread-like elements that are knitted, woven or otherwise integrated with the article of clothing. They may also be applied onto the article of clothing as coatings, as threads sewn thereon, or as loosely applied wires.

The added functionality, i.e. the heating in this example, is activated when the battery 26 is connected to the electrical wires 24.

The principles are the same for other kinds of active articles of clothing, except for that the heating element would be replaced by another functional component and the activation unit would be differently implemented.

From a manufacturing perspective, it may be advantageous to have any functional components and any electrical wires as integrated as possible with the article of clothing so that the manufacturing process can be as similar as possible for active articles of clothing and traditional passive articles of clothing.

Figure 3:
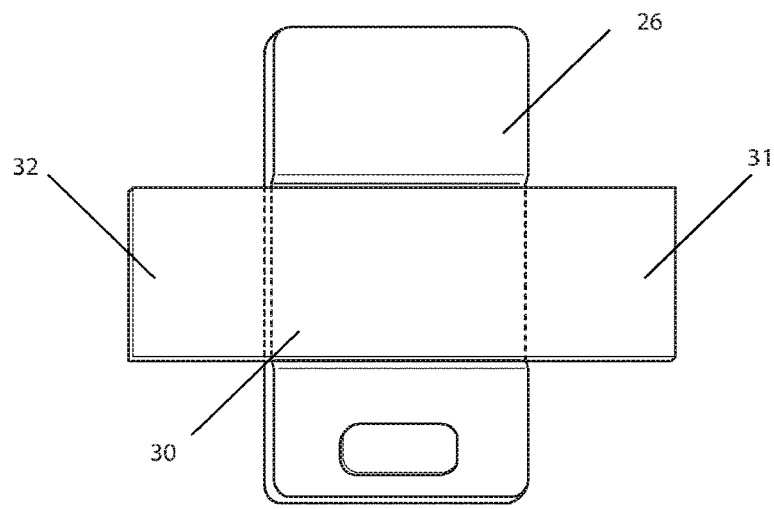

In order for the active article of clothing to be comfortable for the user, the activation unit needs to be secured to the article of clothing. FIG. 3 schematically shows how this can be achieved. A flexible holding element 30 is affixed to an article of clothing (not shown) at two spaced apart locations 31, 32 and the activation unit 26 is held between the holding element and the article of clothing.

Figure 4:
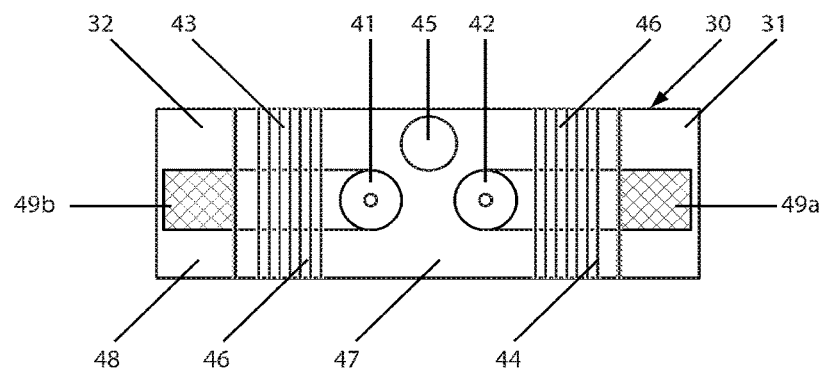
FIG. 4 schematically shows a holding element to be used together with an article of clothing, FIG. 5 schematically shows an activation unit.

FIG. 4 schematically shows one example of how the holding element 30 may be designed at its inside, i.e. at the side that is intended to face the article of clothing when the holding element is affixed thereto.

The holding element has two main purposes: To secure the activation unit to the article of clothing and to electrically connect the activation unit to the article of clothing.

In order to secure the activation unit to the article of clothing, the holding element 30 is flexible so that it shapes itself around the activation unit 26 when the activation unit is introduced between the holding element and the article of clothing. The flexibility of the holding element may be achieved in different ways, either by means of the material included in the holding element or by the structure of the holding element or by a combination thereof. The holding element may for instance be of an elastic material or include grooves that allow the holding element to flex. Also, when the article of clothing is used without the activation unit, the holding element may be flattened and will not disturb the ordinary use of the article of clothing.

With regard to the conductive properties of the holding element, it may be made from almost any material with no or low conductivity, so that electrically conductive paths and terminals may be included in the holding element. In one embodiment the holding element is made from a piece of textile material, which could be synthetic or natural. In another embodiment it is made from a continuous material, e.g. from a plastic film. Other examples of conceivable material would include plastic, silicone and Kevlar®.

In FIGS. 3 and 4, the shape of the holding element 30 is rectangular. In other embodiments the holding element may have a different geometry, different proportions, and be of a different size.

In the embodiment shown in FIG. 4, the holding element is made of two layers. An outer layer 48 which is to be facing away from the article of clothing, and an inner layer 47 which is to be facing the article of clothing when the holding element is affixed thereto. The outer layer is somewhat larger than the inner layer. The layers may be molded together.

The holding element is provided with two sets of electrical terminals. The first set of electrical terminals 41, 42 are provided on the inside of the holding element such that they are accessible for electrical connection to the activation unit when the activation unit is held between the holding element and the article of clothing.

The second set of electrical terminals 49a, 49b are used for electrically connecting the activation unit 26 to the functional component of the article of clothing. They are provided on the inside of the holding element at two places where the holding element is to be affixed to the article of clothing.

The first and second electrical terminals may be in the form of electrical contacts or simply be areas or points accessible for creating an electrical connection.

The holding element 30 includes electrically conductive material that creates electrically conductive paths 43, 44 between the first and second terminals 41, 42 and 49a, 49b, one electrically conductive path from each terminal. These electrically conductive paths 43, 44 may be created by integrating conductive material into the holding element or applying electrically conductive material thereto. The electrically conductive material may for instance be in the form of threads, thread-like elements, a wire, a film or a thin plate or sheet. The material may be a non-corrosive metal or conductive plastic fibers.

In one embodiment where the holding element is a piece of textile material, electrically conductive threads or thread-like elements, may be integrated in the holding element by woving, knitting, sewing or the like.

In another embodiment where the holding element is of continuous material, the electrically conductive material may be integrated in the holding element between two layers of material, but made accessible at places where electrical contact is to be made with the article of clothing.

In the embodiment shown in FIG. 4, a mesh of electrically conductive threads forms each conductive path 43, 44 from the first electrical terminals 41, 42 to a place close to the short end of the holding element where the end of the conductive path forms the second electrical terminal 49a, 49b for connection to the article of clothing.

The electrically conductive paths 43, 44 may as an alternative be formed by means of a coating, e.g. electrically conductive ink, or any other separate element of an electrically conductive material that is applied onto the holding element.

As mentioned, the holding element is intended to be affixed to an article of clothing at two spaced apart locations 31, 32, for instance close to the short ends of the holding element. The affixing should be done such that at least a part of each one of the conductive paths 43, 44 of the holding element is electrically connected to electrically conductive material in the article of clothing.

The holding element may be affixed to the article of clothing in different ways, for instance by sewing, riveting or gluing. The holding element may be affixed to the article of clothing in more locations than two. The holding element may for instance be affixed to the article of clothing at its lower edge in order to form a pocket-like structure to strengthen the support of the activation unit.

There is no specific requirement on the form or size of the conductive paths 43, 44 other than that they should be suitable for creating electrical contact between the terminals 41, 42 and the article of clothing. In FIG. 3 they are shown as bands of constant width ending at the short sides of the holding element. In order to increase the area of connection and lessen the required precision for affixation to the article of clothing, the conductive paths may for instance be made broader towards the ends of the conductive paths. They may but need not extend to the edges of the holding element.

In the embodiment shown in FIG. 4, the conductive paths end and form the second electrical terminals 49a, 49b at places close to the two short sides of the holding element. In another embodiment, the second electrical terminals 49a, 49b are placed close to a same edge of the holding element. As is evident from above, the activation unit 26 is secured to the article of clothing by being enclosed or surrounded by the holding element 30.

The holding effect of the holding element may be reinforced by means of the first electrical terminals. In addition to being designed for electrical connection, they may also be designed for securing the activation unit to the holding element. The electrical terminals 41, 42 of the holding elements and those 52, 53 of the activation unit 26 may for instance be kept together by a magnetic force, by a mechanical grip or by a friction force. The stronger the holding effect of the electrical terminals, the weaker the holding effect of the holding element may be, and vice versa.

In order to simplify the connection of the activation unit 26 to the electrical terminals of the holding element, the material between the terminals may be non-resilient so as to keep the distance between the terminals constant, whereas other parts of the holding element may be of resilient or flexible material to increase the holding effect of the holding element or include structures to improve the flexibility, like grooves 46 in FIG. 4. The holding element 30 may be provided with an identification tag 45 that can be read by the activation unit. In one embodiment, the holding element can be provided with a code, e.g. a color code or a barcode, that can be optically read. In another embodiment the identification tag may be an electronic identification tag, such as an RFID (Radio Frequency Identification) or a NFC (Near Field Communication) tag. The identification tag may identify the type of article of clothing, e.g. making it possible to distinguish a sock from a glove, or the model or version of the article of clothing, e.g. making it possible to distinguish a ski sock from a trekking sock or a left sock from a right sock. In one embodiment the ID is unique for each individual item of clothing.

The ID may be used in the activation unit for selecting parameters, threshold levels, and/or programs to be used for the active article of clothing identified by the ID.

The outside of the holding element 30 may be even. It may be used as an area for a brand or trademark.

The holding element 30 may be designed to look similar to the kind of labels that are affixed to traditional garments for providing the user with information about the garment and how it should be cared for. An alternative name for the holding element could therefore be a "label".

The holding element 30 may be used in the same way on different kinds of articles of clothing. Thus one and the same activation unit 26 may be moved between different articles of clothing for use at different occasions.

The active articles of clothing and the holding elements may be separately manufactured. If the elements for the active function of the article of clothing are integrated into the article of clothing, such as for instance when a heating element and connections thereto are formed by conductive threads that are knitted or woven in the same way as the other parts of the product, an active article of clothing may be manufactured in the same way as a traditional article of clothing. The holding element may then be affixed to the article of clothing afterwards.

Figure 5:
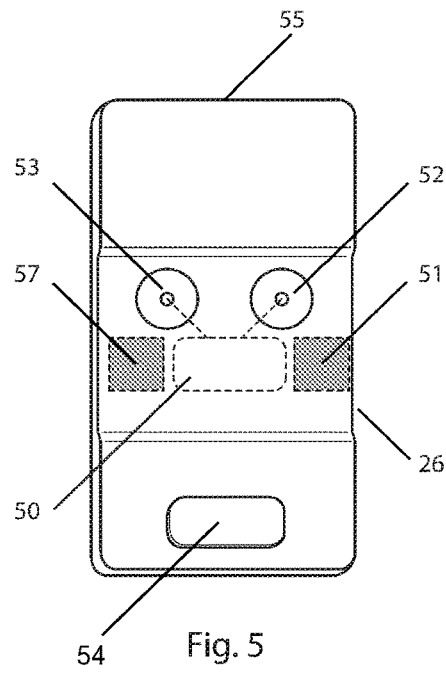

FIG. 5 schematically shows an activation unit 26 to be used for an active article of clothing seen from the front side that will face the inside of the holding element when held by the holding element. In one embodiment, the activation unit comprises one or more batteries 50, which may be rechargeable, e.g. lithium-ion batteries. The one or more batteries may be removable from the activation unit for recharging or they may be rechargeable in the activation unit. In another embodiment the activation unit comprises a power pack that converts the current from the one or more batteries to a current that is suitable for the functional component(s) of the active article of clothing. The one or more batteries may be used for powering a functional component of an active article of clothing, and/or for supplying and receiving electrical signals to and from a functional component in an active article of clothing.

In one embodiment the activation unit 26 comprises a control module 51 that controls the operation of the active article of clothing. In the case of an actively heatable article of clothing, the control module may control the amount of energy output from the activation unit. If the article of clothing is of a kind where the resistance of the heating element and any connections thereto may vary depending on the use of the article of clothing, the control module may measure the resistance and control the energy output in response thereto. If the article of clothing includes one or more sensors, the control module may for instance control the retrieval of measurement data. The control module may be implemented by means of a microprocessor.

As already mentioned, the activation unit includes electrical terminals 52, 53, which are connected directly or indirectly to the one or more batteries 50 and which are intended to be connected to the electrical terminals of the holding element 30.

The activation unit 26 may include one or more controls 54 for manual control of the activation unit. It may for instance be provided with a multi-function push button or knob or similar means for turning on and off the unit and for setting different function modes. For an actively heated garment different heating levels may be manually set by the user using the controls.

The activation unit may furthermore include feed-back means for giving feed-back to a user, for instance, a buzzer, a vibrator, visual or audio indicators or a display for displaying information about settings, the charging level of the battery, different measurement data and the like.

The housing 55 of the activation unit may be designed to simplify and reinforce the securing of the activation unit to the article of clothing. In one embodiment the housing has a waist portion 56, i.e. a portion with a smaller thickness, where the holding element is intended to encircle the activation unit when held by the holding element.

In one embodiment, the activation unit may be remotely controlled from a dedicated or general remote control. For that purpose the activation unit may include a communications module 57 for wireless communication with the remote control. The activation unit may for instance include a Bluetooth® module. In one embodiment, the control module 51 and the communications module 57 are implemented by a Bluetooth 4 module. The remote control function may be realized by a software application in a smart phone.

The remote control may include means for turning on and off the activation unit and to make the same settings as can be done manually on the activation unit.

In one embodiment, the remote control may be used for controlling more than one activation unit on one or more articles of clothing. As one example, a user may have a pair of actively heatable socks with one activation unit on the left sock and one on the right sock. The remote control can then be used for making the same settings for both socks or a different setting for each one of the socks.

When a user make settings for an active article of clothing it may be difficult for the user to know whether the charging in the activation unit will suffice for the whole intended period of use. To solve this problem, the user may instead set the intended time of use, and a calculating module in the remote control or in the activation unit will calculate the levels of the setting(s) based on the current amount of charge in the battery in the activation unit and the intended time of use set by the user.

The remote control and/or the activation unit may furthermore be adapted to vary the heating level depending on the motion by the user. The activation unit and/or the remote control may for this purpose be provided with one or more accelerometers which measure the movements of the user. Different threshold values may be used to control the increase or decrease of the energy output from the activation unit. A higher output may be needed when the user is relatively still, for instance going up by a ski lift, compared to when the user is moving, e.g. skiing down a slope. When a smart phone is used for the remote control, its built-in accelerometer may be utilized for this function.

The above described ideas for setting and controlling the active articles of clothing may of course be used independently of how the activation unit is designed and how it is secured to the article of clothing.

Figure 6:
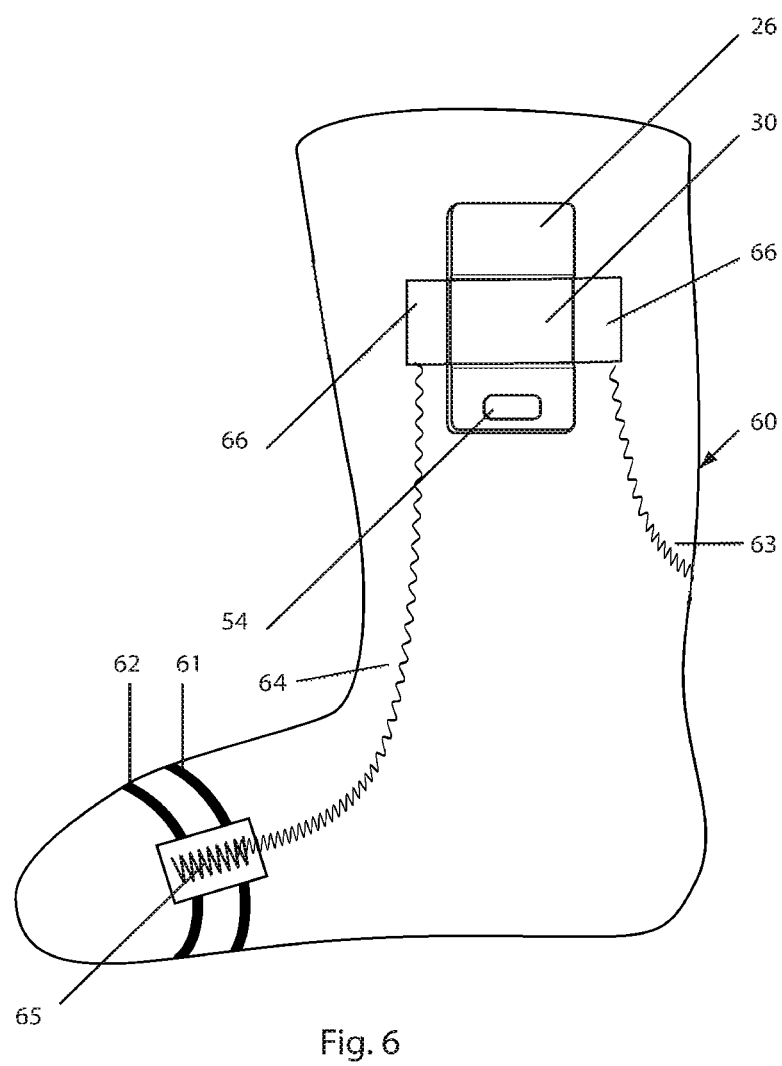
FIG. 6 schematically shows an actively heated sock provided with a holding element and an activation unit.

FIG. 6 shows an example of an actively heatable sports sock provided with a holding element 30 and an activation unit 26. The sock is of a knitted material. Heating elements 61, 62 are integrated parts of the sock. They are created by portions of the sock knitted by an electrically conductive thread with high resistance. The sock has two zig-zag seams 63, 64 that act as connectors between the heating elements and the holding element. The zig-zag seams are sown onto the sock and include an electrically conductive thread with low resistance. Each seam extends from a connecting area 65 (only one shown) at the heating elements 61, 62 to one of two connecting areas 66 where the holding element is affixed. The connecting areas 65, 66 may be portions of the sock knitted by a low-resistive conductive thread, but may also be just the areas where the zig-zag seams connect to the holding element/heating elements. The activation unit 26 is held by the holding element 30. Its first set of electrical terminals 41, 42 are connected to the electrical terminals 52, 53 of the holding element. One terminal in each pair includes a magnet so that the pair of terminals are kept together by a magnetic force. A press-button 54 on the activation unit is accessible for the user below the holding element so that the user can turn on and off the heating and set the desired level of heating. When the heating is activated, current flows from the activating unit, through the one pair of activation unit-holding element electrical terminals, through the corresponding conductive path of the holding element, to the connecting field of the sock, and further through the zig-zag seam to the connecting portion at the heating elements, through the heating elements where heat is created and back the corresponding way to the battery.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A holding element to be affixed to an active article of clothing, which includes at least one component that is intended to be electrically connected to an activation unit, which is to be secured to the article of clothing by the holding element, wherein the holding element is intended to be affixed to the article of clothing at two spaced apart locations;

the holding element is provided with first electrical terminals for connection to the activation unit, second electrical terminals for connection to the at least one component of the active article of clothing, and electrically conductive paths between the first and second electrical terminals; and the second electrical terminals being placed where the holding element is intended to be affixed to the article of clothing, wherein the holding element is arranged to hold the activation unit between the holding element and the article of clothing between the two spaced apart locations; and the holding element is flexible, so that it shapes itself around the activation unit when the activation unit is introduced between the holding element and the article of clothing.

2. A holding element according to claim 1, wherein the first electrical terminals are further designed for securing the activation unit to the holding element.

3. A holding element according to claim 1, wherein the holding element is made of flexible material or includes structure that allows it to flex.

4. A holding element according to claim 1, wherein the electrically conductive paths are created by means of a non-corrosive metal mesh.

5. A holding element according to claim 1, wherein it further comprises an identification tag, which makes it possible to distinguish the article of clothing from at least one other article of clothing.

6. A holding element according to claim 1, wherein the second electrical terminals are placed at the two spaced apart locations where the holding element is intended to be affixed to the article of clothing.

7. A holding element according to claim 1, wherein the material between the first electrical terminals is non-resilient, whereas the material of at least one other part of the holding element is resilient.

8. A holding element according to claim 1, wherein the first electrical terminals are located at the side of the holding element that is intended to face against the article of clothing when affixed to the article of clothing.

9. An active article of clothing, which includes at least one component that is intended to be electrically connected to an activation unit, wherein a holding element according to claim 1 is affixed to the article of clothing at two spaced apart locations at least one of which includes electrically conductive material so that electricity can be transferred between the conductive paths of the holding element to the electrically conductive material in the article of clothing.

10. An article of clothing according to claim 9, wherein the at least one component is a heating element.

11. An article of clothing according to claim 9, wherein the first electrical terminals are located at the side of the holding element that faces against the article of clothing.

12. A kit including an active article of clothing according to claim 9 and an activation unit, which is designed to be held between holding element and the article of clothing and which has electrical terminals for connection to the first electrical terminals of the holding element.

* * * * *